United States Patent
Martinez-Orgado et al.

(10) Patent No.: US 10,220,005 B2
(45) Date of Patent: Mar. 5, 2019

(54) SYNERGISTIC THERAPIES OF CANNABIDIOL WITH HYPOTHERMIA FOR NEUROPROTECTION

(71) Applicant: GW Research Limited, Histon, Cambridge, Cambridgeshire (GB)

(72) Inventors: Jose Martinez-Orgado, Madrid (ES); Geoffrey Guy, Cambridgeshire (GB)

(73) Assignee: GW Research Limited, Histon, Cambridge, Cambridgeshire (GB)

( * ) Notice: Subject to any disclaimer, the term of this patent is extended or adjusted under 35 U.S.C. 154(b) by 156 days.

(21) Appl. No.: 14/405,950

(22) PCT Filed: Jun. 10, 2013

(86) PCT No.: PCT/GB2013/051519
§ 371 (c)(1),
(2) Date: Dec. 5, 2014

(87) PCT Pub. No.: WO2013/182862
PCT Pub. Date: Dec. 12, 2013

(65) Prior Publication Data
US 2015/0148872 A1  May 28, 2015
US 2015/0328171 A2  Nov. 19, 2015
US 2016/0243054 A2  Aug. 25, 2016

(30) Foreign Application Priority Data
Jun. 8, 2012 (GB) .................................. 1210142.4

(51) Int. Cl.
*A61F 7/00* (2006.01)
*A61K 31/05* (2006.01)
*A61K 36/185* (2006.01)
*A61F 7/02* (2006.01)

(52) U.S. Cl.
CPC ................ *A61K 31/05* (2013.01); *A61F 7/00* (2013.01); *A61K 36/185* (2013.01); *A61F 7/02* (2013.01); *A61F 2007/0056* (2013.01)

(58) Field of Classification Search
CPC .. A61K 31/05; A61K 2300/00; A61K 36/185; A61F 2007/0056; A61F 7/00; A61F 7/02
See application file for complete search history.

(56) References Cited

FOREIGN PATENT DOCUMENTS

GB       2 434 312 A      7/2007
WO   WO 2009071096 A2 *  6/2009  .......... A61K 31/165

OTHER PUBLICATIONS

Maria Roberta Cilio, Donna M. Ferriero ,Synergistic neauroprotective with hypothermia, Oct. 2010, Elsevier, vol. 15, pp. 293-298.*

(Continued)

*Primary Examiner* — Kaitlyn Smith
*Assistant Examiner* — Tigist Demie
(74) *Attorney, Agent, or Firm* — Wolf, Greenfield & Sacks, P.C.

(57) ABSTRACT

The present invention relates to a method of treating newborn hypoxic-ischemic encephalopathy (NHIE). Such method comprises administering the phytocannabinoid cannabidiol (CBD) in combination with therapeutic hypothermia to a newborn subject suffering from NHIE. Preferably the CBD is in the form of a plant extract, alternatively the CBD is in a pure or isolated form.

3 Claims, 3 Drawing Sheets

(56) References Cited

OTHER PUBLICATIONS

Alvarez et al., Neuroprotective effects of the nonpsychoactive cannabinoid cannabidiol in hypoxic-ischemic newborn piglets. Pediatr Res. Dec. 2008;64(6):653-8. doi:10.1203/PDR.0b013e318186e5dd.

Castillo et al., The neuroprotective effect of cannabidiol in an in vitro model of newborn hypoxic-ischemic brain damage in mice is mediated by CB(2) and adenosine receptors. Neurobiol Dis. Feb. 2010;37(2):434-40. doi: 10.1016/j.nbd.2009.10.023.

Hobbs et al., Xenon and hypothermia combine additively, offering long-term functional and histopathologic neuroprotection after neonatal hypoxia/ischemia. Stroke. Apr. 2008;39(4):1307-13. doi: 10.1161/STROKEAHA.107.499822.

Kim et al., Therapeutic hypothermia in brain injuries and related diseases. Recent Patents on Inflammation & Allergy Drug Discovery. May 2011;5(2):155-64.

Lafuente et al., Cannabidiol reduces brain damage and improves functional recovery after acute hypoxia-ischemia in newborn pigs. Pediatr Res. Sep. 2011;70(3):272-7. doi: 10.1038/pr.2011.497.

Marion et al., Current and future role of therapeutic hypothermia. J Neurotrauma. Mar. 2009;26(3):455-67. doi: 10.1089/neu.2008.0582.

Ohmura et al., Prolonged hypothermia protects neonatal rat brain against hypoxic-ischemia by reducing both apoptosis and necrosis. Brain Dev. Oct. 2005;27(7):517-26.

Pazos et al., Cannabidiol administration after hypoxia-ischemia to newborn rats reduces longterm brain injury and restores neurobehavioral function. Neuropharmacology. Oct. 2012;63(5):776-83. doi: 10.1016/j.neuropharm.2012.05.034. Epub May 30, 2012.

Perrone et al., New pharmacologic and therapeutic approaches for hypoxic-ischemic encephalopathy in the newborn. J Matern Fetal Neonatal Med. Apr. 2012;25 Suppl 1:83-8. doi: 10.3109/14767058.2012.663168. Epub Mar. 6, 2012.

Thoresen et al., Therapeutic hypothermia for hypoxic-ischaemic encephalopathy in the newborn infant. Curr Opin Neurol. Apr. 2005;18(2):111-6.

Pertwee, The diverse CB1 and CB2 receptor pharmacology of three plant cannabinoids: delta9-tetrahydrocannabinol, cannabidiol and delta9-tetrahydrocannabivarin. Br J Pharmacol. Jan. 2008;153(2):199-215. Epub Sep. 10, 2007.

* cited by examiner

SYNERGISTIC THERAPIES OF CANNABIDIOL WITH HYPOTHERMIA FOR NEUROPROTECTION

RELATED APPLICATION

This application is a national stage filing under 35 U.S.C. § 371 of international application PCT/GB2013/051519, filed Jun. 10, 2013, which was published under PCT Article 21(2) in English.

The present invention relates to the use of the phytocannabinoid cannabidiol (CBD) in combination with other therapies that are useful in neuroprotection. Preferably the other therapy is hypothermia. In a further embodiment the combination treatment of hypothermia and CBD may additionally include further treatments that are useful in neuroprotection. Such therapies include anti-epileptic drugs; xenon; N-acetylcysteine; erthyropoietin, and melatonin. Preferably the neuroprotective therapies are used in the treatment of hypoxic-ischemic encephalopathy (HIE), more preferably the HIE is newborn hypoxic-ischemic encephalopathy (NHIE), stroke or cardiac arrest.

BACKGROUND TO THE INVENTION

Perinatal asphyxia resulting in newborn hypoxic-ischemic encephalopathy (NHIE) occurs in between 2 to 9/1000 live term newborns. A vastly higher number of preterm babies (60/1000 live preterm babies) also suffer from this condition. In addition to inflicting direct brain damage, leading to acute brain dysfunction, such an insult can also interfere with brain development, determining long-term morbidity.

Worldwide approximately 2 million babies die or remain with long-lasting disability because of NHIE each year.

Despite the continuous progress in Neonatology and Perinatology recently, the aforementioned numbers have not substantially changed. Thus, NHIE remains as the main cause of acquired neonatal neurological impairment of babies worldwide.

Management of NHIE is determined by its complex pathophysiology. After the early energetic fall during hypoxia-ischemia, failure of neuronal ionic pumps lead to a toxic increase of intracellular calcium, activating degrading enzymes. There is also an increase in extracellular excitotoxic substances such as glutamate, which further increases calcium influx.

During reperfusion, re-oxygenation and inflammatory responses start a second wave of damage, which lead to a secondary energetic failure and to DNA damage, activating apoptosis.

Substances within the body such as heat shock proteins, antiapoptotic proteins, neural growth factors and endocannabinoids are able to act as natural neuroprotective and neuro-regenerative substances. However in the majority of cases lack of treatment results in severe brain damage or death.

The immature brain is particularly susceptible to hypoxic-ischemic damage because of a higher sensitivity to glutamate, cytokines and oxidative stress, and the preponderance of pro-apoptotic mechanisms.

Hypoxic-ischemic (HI) damage may affect the fetus at various stages of fetal development, or it can affect the newborn during labour and delivery and in the postnatal period.

Problems during pregnancy may include preeclampsia, maternal diabetes with vascular disease, congenital fetal infections, drug/alcohol abuse, severe fetal anemia, cardiac disease, lung malformations, or problems with blood flow to the placenta.

Problems during labour and delivery can include umbilical cord occlusion, torsion or prolapse, rupture of the placenta or uterus, excessive bleeding from the placenta, abnormal fetal position such as the breech position, prolonged late stages of labour, or very low blood pressure in the mother.

Problems after delivery can include severe prematurity, severe lung or heart disease, serious infections, trauma to the brain or skull, congenital malformations of the brain, or very low blood pressure in the baby.

There is a "temporary therapeutic window" between the HI insult and the irreversible secondary energetic failure, which determines the possibility of a therapeutic strategy leading to the reduction of HI brain damage. Such a strategy has to act on several factors, including excitotoxicity, oxidative stress and inflammation.

Therapeutic hypothermia has been demonstrated to be a useful treatment of NHIE and has become the only therapy with a proven neuroprotective effect in human newborns. Unfortunately, these benefits are partial and only successful in mild cases.

Recent clinical trials in newborns have demonstrated that induced moderate hypothermia reduces the combined outcome of mortality and long-term neurodevelopmental disability at 12-24 months of age. Aside from hypothermia, no established therapies exist.

Hypothermia does not completely protect an injured brain; newborns with the most severe forms of HI injury are often not successfully treated.

The addition of other therapies added during or after hypothermia that can improve neuroprotection, by extending the therapeutic window or providing long-lasting additive or synergistic protection, are needed (Cilio and Ferriero, 2010). However it is important to consider that drugs administered during the neonatal period may be toxic to the immature brain. Excretion of many drugs and their metabolites can be modified by hypothermia, and thus failure of liver and kidney clearance due to HI injury could exacerbate any toxicity.

Anti-epileptic drugs (AED) have been used in combination with hypothermia mainly because seizures are commonly associated with HIE. The AED Topiramate has shown some synergy with hypothermia in animal models if used immediately after the HI event, however the dose used was well above that used for treatment of epilepsy in children.

Indeed Cilio and Ferriero suggest agents such as xenon; N-acetylcysteine; erthyropoietin, melatonin and cannabinoids might augment the protection from hypothermia.

The applicant proposed that since cannabinoids reduce calcium influx and glutamate release, are antioxidant and anti-inflammatory substances, modulate MAP kinase pathways, induce hypothermia and promote neuro-regeneration they might be used in the treatment of NHIE. Many of these effects, however, are due to CB1 receptor activation. In immature brains, over activation of CB1 receptors is known to increase apoptosis. Thus, CB1 agonists are not suitable for neuroprotection in NHIE.

The non-psychoactive cannabinoid cannabidiol (CBD) is of great interest because its effects are CB1-independent. Indeed CBD has been shown to reduce histological and biochemical brain damage in in vivo and in vitro models of NHIE (Alvarez et al., 2008). This cannabinoid has also been shown to provide beneficial effects for at least 3 days post the HI event (Lafeunte et al., 2011).

Additionally the United Kingdom patent GB 2,434,312 describes the neuroprotective properties of a CBD plant extract.

Currently the lack of useful treatments to augment therapeutic hypothermia mean a considerable financial and lifelong personal burden on society and the affected families of newborns suffering from NHIE. Therefore there is an urgent need to improve the outcome for these infants.

Surprisingly, the combination of therapeutic hypothermia with the cannabinoid CBD has been shown to be synergistic in neuroprotection following HI injury in an animal model of NHIE, and as such offers a beneficial treatment option for NHIE.

BRIEF SUMMARY OF THE DISCLOSURE

In accordance with a first aspect of the present invention there is provided a combination of the phytocannabinoid cannabidiol (CBD) with therapeutic hypothermia for use in the treatment of hypoxic ischemia.

Preferably the CBD is in the form of a plant extract. Alternatively the CBD is in a pure or isolated form.

Preferably the hypoxic ischemia to be treated is newborn hypoxic-ischemic encephalopathy (NHIE).

Alternatively the hypoxic ischemia to be treated is a stroke or a cardiac arrest.

BRIEF DESCRIPTION OF THE DRAWINGS

Embodiments of the invention are further described hereinafter with reference to the accompanying drawings, in which.

DETAILED DESCRIPTION

Figure 1A:
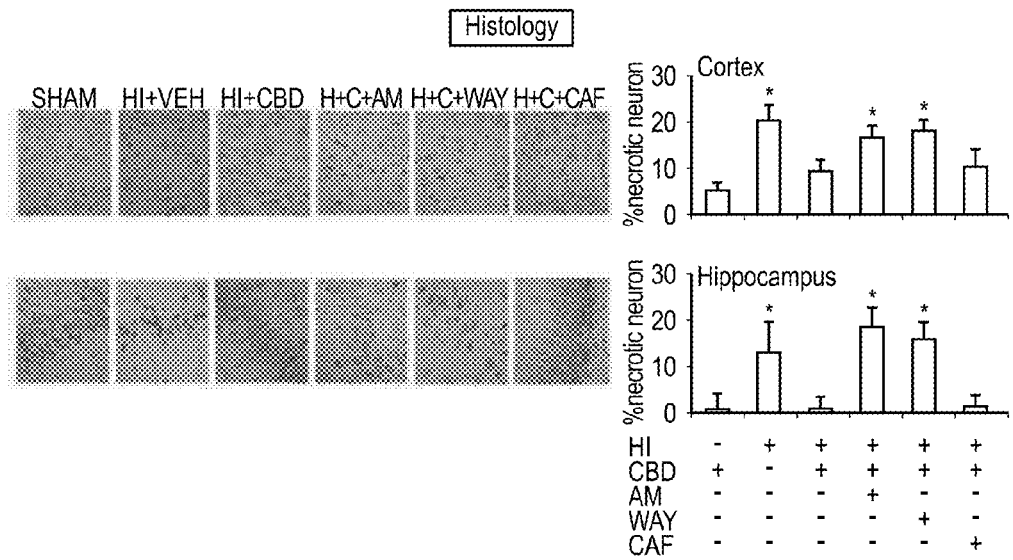
FIG. 1 shows the histology of piglet brains treated after HI injury.

Example 1 below demonstrates the prior art and details the neuroprotective properties of CBD in two different models. It is demonstrated that the CBD enables repair of brain tissue after an HI injury.

Example 2 demonstrates the synergistic neuroprotective effect of CBD with therapeutic hypothermia.

EXAMPLE 1

Neuroprotective Properties of Cannabidiol (CBD) Following Hypoxic-Ischemica (HI)

Materials and Methods

A piglet model of HI was used as described in (Alvarez et al. 2008). Briefly, an HI insult is induced in anesthetized 1-3 day-old piglets by occluding both carotid arteries and decreasing inspired oxygen from 21 to 10% for 30 min.

Thirty minutes after the recovery of HI the test compound was administered via the i.v. route. The test compounds were:
Vehicle;
CBD (1 mg/kg);
CBD (1 mg/kg) plus AM630 which is a CB2 antagonist (1 mg/kg);
CBD (1 mg/kg) plus WAY100635 which is a 5HT1A antagonist (0.1 mg/kg); or
CBD (1 mg/kg) plus Caffeine which is a non-specific adenosine receptor antagonist (10 mg/kg).

Hemodynamic parameters (cardiac output, blood pressure, heart rate and extravascular lung water content), temperature, respiratory parameters (lung compliance, airway resistance, oxygenation index) were recorded for 6 hours from the end of HI.

Blood samples were obtained hourly and urine was collected. Brain activity was recorded by amplitude-integrated EEG.

At the end of the experiment, piglets are euthanized and the brain removed; one hemisphere was immediately frozen and stored at $-80\,^\circ$ C. whereas the other one was preserved in 4% paraformaldehide. A sample of frozen brain was obtained to perform a proton magnetic resonance spectroscopy (H+-MRS). Similarly managed piglets but without HI served as controls.

Blood samples from CBD-treated piglets were used to determine serum CBD concentration.

A rat model of HI was used as described by (Fernandez-Lopez et al., 2007). Briefly, an HI insult is induced in 7-10 day-old Wistar rats by electro-coagulating the left carotid artery under anaesthesia following by the exposure to 10% oxygen for 120 min.

After the end of HI, pups were treated with 0.1 mL s.c. of vehicle or CBD (1 mg/kg) in a single dose.

Sham operated pups without hypoxia served as controls, and were treated with vehicle or CBD as indicated. The pups were then returned to their dams.

At day 35 rats underwent neurobehavioral tests: rotarod (to test coordination), cylinder (to test unilateral deficits) and novel object preference (to test memory impairments).

Rats were then euthanized and the brain removed and stored in 4% paraforlmadehide. Magnetic resonance imaging was performed on the brains to evaluate the damaged area. In some rats, MRI was performed 7 days after HI.

Results

Piglet Model

Figure 1B:
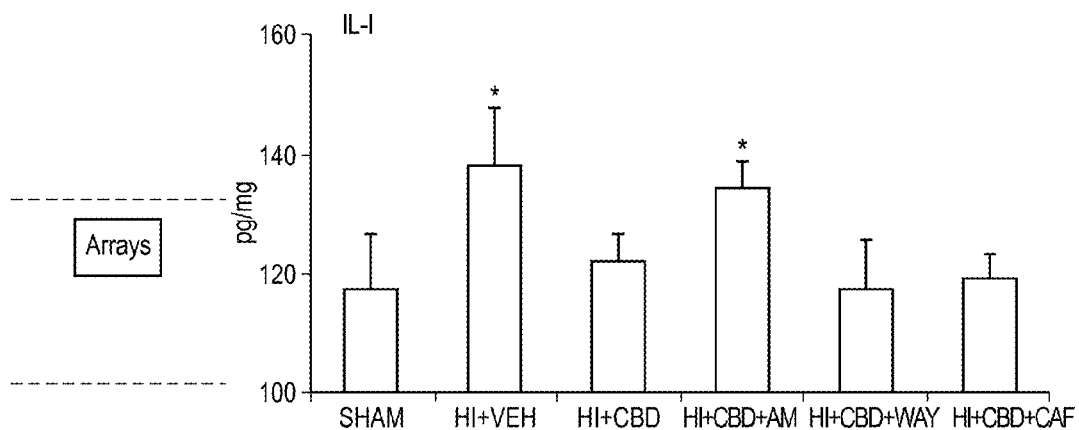

FIG. 1 *a*) and *b*) shows the brain tissue obtained 6 h after the end of hypoxia-ischemia (HI). FIG. 1 *a*) compares Nissl staining of brain slices from sham piglets to those exposed to HI and treated with vehicle or CBD 1 mg/kg i.v., alone or with the CB2 antagonist AM630 (AM), the 5HT1A antagonist WAY100630 (WAY) or the adenosine antagonist caffeine (CAF).

As can be seen CBD reduces the percentage of necrotic tissue in both the cortex and the hippocampus. The CBD-induced reduction of neuronal death is blunted by either AM or WAY, but not by caffeine.

FIG. 1 *b*) shows the concentration of interleukin 1 in brain tissue determined by microarrays. Again CBD reduces the production of IL-1, which is blunted by AM but not by WAY or caffeine.

Rat Model

Figure 2A:
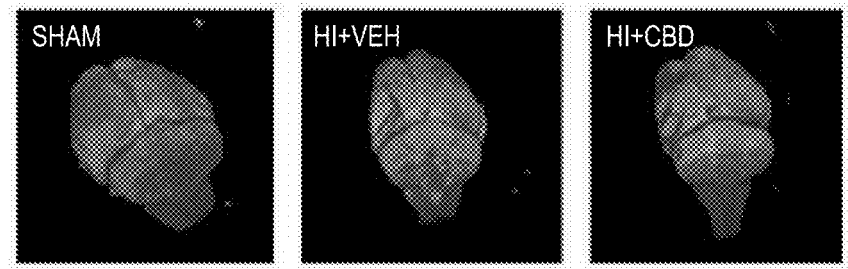
FIG. 2 shows a comparison of brain lesions in rats after HI injury.
Figure 2B:
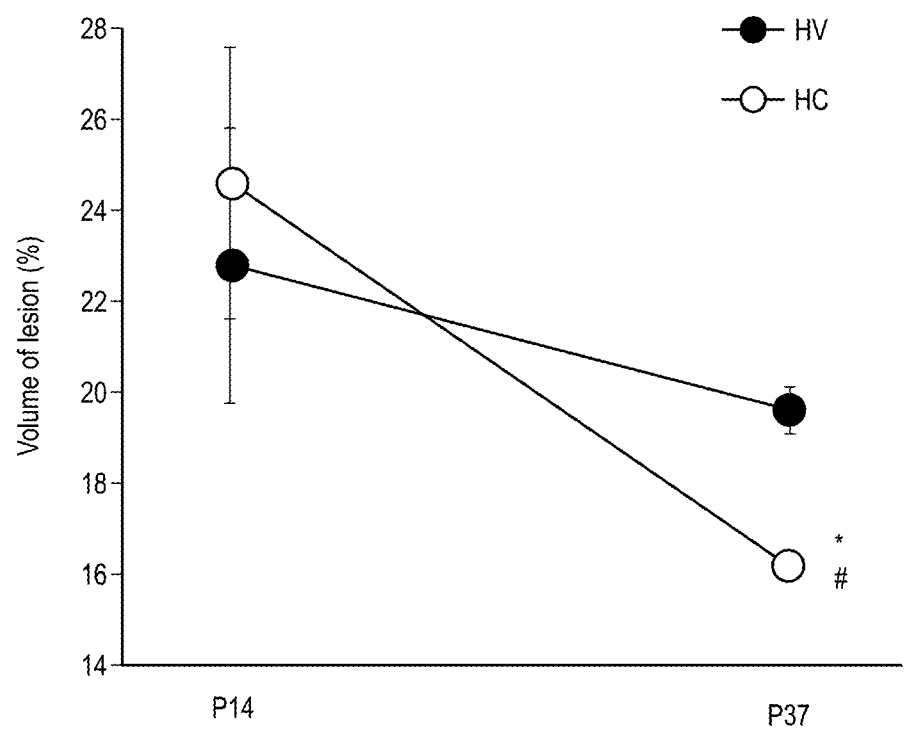

FIG. 2 demonstrate the Magnetic Resonance imaging (MRI) of the rat brains, these revealed that the volume of lesion was similar in HI+VEH and HI+CBD 7 days after HI, suggesting that the severity of brain damage was similarly strong in both groups.

One month later (P37), the brain volume remained similar in HI+VEH but was significantly reduced by CBD.

Figure 3:
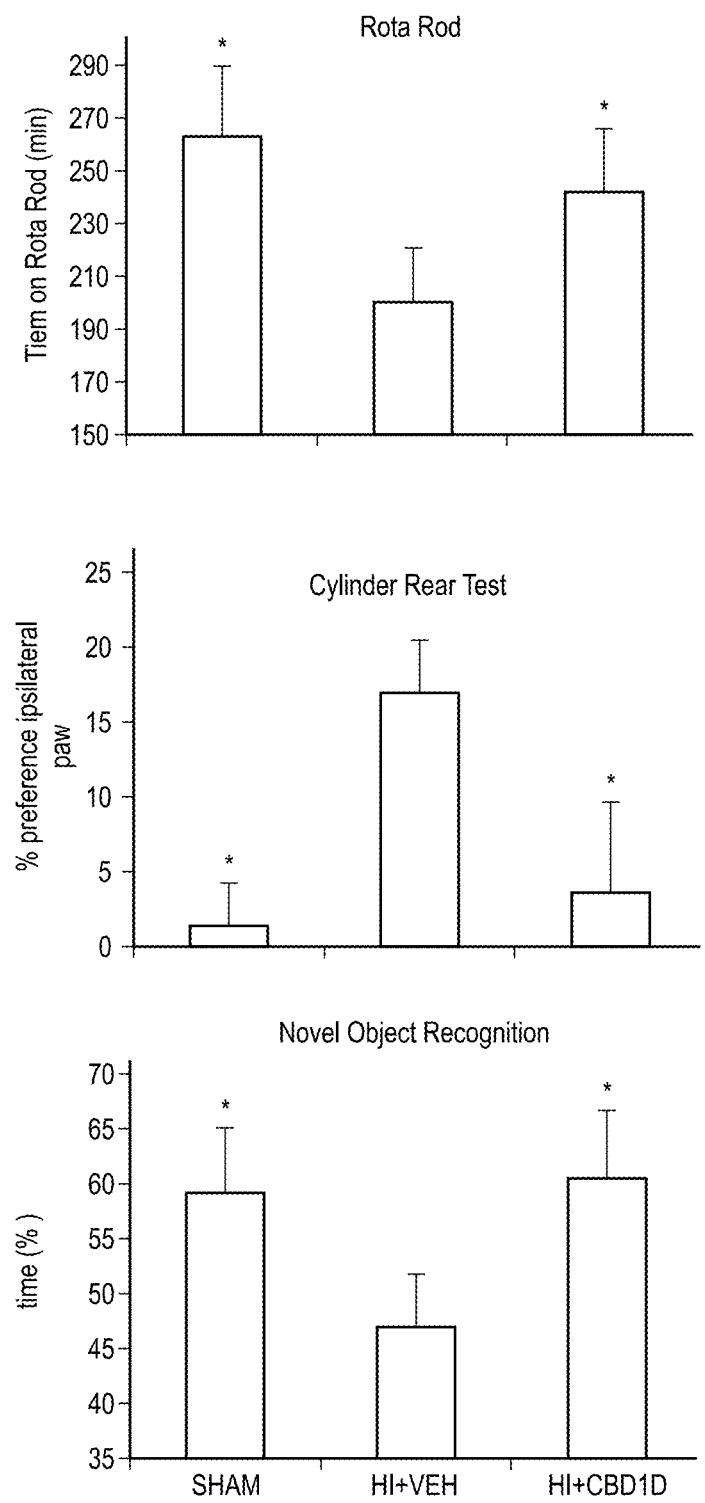
FIG. 3 shows the neurobehavioural performance of rats after HI injury.

FIG. 3 demonstrates the protective effect of CBD included not only the volume of lesion but also the neurobehavioral performance of the rat. CBD administration led to the normalization of motor (cylinder rear test), coordination (RotaRod) and memory (novel object recognition) tests, whereas the untreated rats performed poorly in the neurobehavioral tests.

Conclusion

The piglet model showed that the CBD was able to reduce the amount of necrotic areas in the brain caused by HI.

The rat model showed that CBD is neuroprotective and in addition to this effect a reduction of brain damage was observed after a month. The cannabinoid CBD is stimulating neuro-repair.

EXAMPLE 2

Synergistic Administration of Cannabidiol (CBD) With Therapeutic Hypothermia Following Hypdxic-Ischemica (HI)

Materials and Methods

Sedated and ventilated piglets (1-2 day-old) underwent HI brain damage (hypoxia-FiO2 10%+bilateral carotid artery compression for 30 min).

Normothermic (NT) piglets were maintained at 37-38° C. using a warmed air blanket.

Hypothermic (HT) piglets were cooled by a cool water mattress to 33-34° C.

Thirty min after HI piglets received via the i.v. route either vehicle (VEH) or CBD (1 mg/kg).

HI brains were obtained for histological studies quantifying the number of neurons (Nissl), astrocytes (GFAP) and microglial cells (mGC) (IBA-1) in parietal cortex 6 hours after HI injury.

By dividing the area percentage of GFAP- or IBA-1-immunoreactive processes and cell bodies (ImageJ) by the number of cells, a mean size of astrocytes or mGC was obtained.

Similarly studied animals without HI insult served as controls (Sham, SHM).

Results

Neuronal protection was found to be best in the CBD plus hypothermia treated animals, (p<0.05).

CBD prevented the HI-induced reduction in the number of astrocytes, particularly in the hypothermia treated animals.

CBD also enhanced astrocyte activity (increased processes equals an increased mean size), particularly in CBD plus hypothermia.

Hypothermic treatment reduced the number of microglial cells, with no differences between the vehicle treated animals and those treated with CBD.

Table 2.1 demonstrates the mean size of the microglial cells after HI injury Table 2.1 Size of microglial cells after HI injury

|  |  | Mean size (pixels) |
|---|---|---|
| Normothermic | Control | 102 |
|  | HI injury + Vehicle | 134 |
|  | HI injury + CBD | 127 |
| Hypothermic | Control | 164 |
|  | HI injury + Vehicle | 219 |
|  | HI injury + CBD | 176 |

As can be seen from the table above the microglial cells were activated after HI, increasing their size, this is demonstrated in the normothermic plus vehicle treated animals where the size of pixels increased from 102 to 134 pixels a rise of 32 pixels. Treatment with CBD and hypothermia produced the smallest increase 164 to 176 pixels a rise of just 12 pixels, compared to CBD alone (102 to 127 pixels, a rise of 25 pixels) and hypothermia alone (164 to 219 pixels, a rise of 55 pixels)

Table 2.2 below details the percentage of necrotic neurons found in the cortex of the test animals.

TABLE 2.2

Percentage of necrotic neurons in the cortex of test animals

|  |  | MEAN (%) |
|---|---|---|
| Normothermic | Control | 5.64 |
|  | HI injury + Vehicle | 26.46 |
|  | HI injury + CBD | 8.41 |
| Hypothermic | Control | 1.67 |
|  | HI injury + Vehicle | 13.19 |
|  | HI injury + CBD | 4.51 |

As can be seen treatment with a combination of hypothermia and CBD produced the lowest percentage of necrotic neurons (4.5%) compared to hypothermia alone (13.2%) and treatment with CBD alone (8.4%).

CONCLUSION

CBD administration after HI protects neurons and astrocytes and modulates microglial activation.

Moreover CBD is slightly more effective than hypothermia, but when both therapies are used in combination statistically significant neuroprotective effects occur.

This synergy provides a useful treatment option in newborns suffering from NHIE. In addition such treatments could be used effectively in the treatment of other human patients suffering from hypoxic ischemic events or diseases such as stroke or cardiac arrest.

REFERENCES

CILIO and FERRIERO, Synergistic neuroprotective therapies with hypothermia, *Semin Fetal Neonatal Med.* October 2010; 15(5): 293-298.

The invention claimed is:

1. A method for treatment of newborn hypoxic-ischemic encephalopathy (NHIE) comprising administering to a newborn human suffering from NHIE a combination of cannabidiol (CBD) with therapeutic hypothermia, wherein the CBD is a non-CB1 agonist.

2. The method as claimed in claim 1, wherein the CBD is in the form of a plant extract.

3. The method as claimed in claim 1, wherein the CBD is in a pure or isolated form.

* * * * *